United States Patent [19]

Carter

[11] 4,053,281
[45] Oct. 11, 1977

[54] METHOD AND APPARATUS FOR DETERMINING ORGANIC CARBON IN SULFUREOUS COMPOUNDS

[75] Inventor: Melvin Keith Carter, Saratoga, Calif.

[73] Assignee: Envirotech Corporation, Menlo Park, Calif.

[21] Appl. No.: 545,853

[22] Filed: Jan. 31, 1975

[51] Int. Cl.$^2$ ........................................... G01N 31/12
[52] U.S. Cl. ........................ 23/230 PC; 23/253 PC
[58] Field of Search .................. 23/230 PC, 253 PC

[56] References Cited

U.S. PATENT DOCUMENTS

| 2,736,638 | 2/1956 | McConnaughey | 23/232 R |
| 3,346,342 | 10/1967 | Miller | 23/253 PC |
| 3,451,779 | 6/1969 | Hozumi | 23/253 PC |
| 3,698,869 | 10/1972 | Condon | 23/230 PC X |
| 3,753,656 | 8/1973 | Matson et al. | 23/232 E |
| 3,762,878 | 10/1973 | Villalobos | 23/232 E |
| 3,861,874 | 1/1975 | Krc | 23/230 PC |

OTHER PUBLICATIONS

Aloe Scientific Catalog 103; 1952; p. 1010.
Merck Index 7th ed., 1960, p. 303.

*Primary Examiner*—Robert M. Reese
*Attorney, Agent, or Firm*—Robert E. Krebs; Hal J. Bohner

[57] ABSTRACT

Measured sample quantities of sulfureous matter are introduced into a sealed chamber where the samples are pyrolyzed to form sulfur dioxide and sulfur trioxide gases and to oxidize organic substances to form carbon dioxide gas. The gases are then passed through a free sulfur-absorbing packing and into a scrubbing zone wherein transition metal amine complex is used to remove sulfureous compounds without reaction with the carbon dioxide gas. The scrubbed gases are then analyzed to determine the carbon dioxide content thereof.

13 Claims, 1 Drawing Figure

METHOD AND APPARATUS FOR DETERMINING ORGANIC CARBON IN SULFUREOUS COMPOUNDS

BACKGROUND OF THE INVENTION

1. FIELD OF THE INVENTION

This invention generally relates to automatic ways and means for determining the quantity of organic carbon in sulfureous compounds, such as sulfuric or sulfurous acids.

2. STATE OF THE ART

Various manufacturing and processing operations require the usage of high-purity sulfureous mixtures and compounds. For instance, it is typically required that the sulfuric acid utilized in the production of beverage chemicals contain less than 50 parts per million of organic carbon compounds. Sulfuric acid is also used in electro-plating processes, especially copper and chrome plating, where it is conventional practice to add quantities of organic carbon compounds to a sulfuric acid bath to achieve various plating characteristics such as brightness. Heretofore, however, there have been no available means for continuously and immediately determining quantitatively the trace quantities of organic carbon in such compounds and mixtures.

OBJECTS OF THE INVENTION

An object of this invention is to provide improved ways and means for analyzing sulfureous mixture or compounds to determine their organic carbon content.

A more specific object is to provide ways and means for eliminating sulfur from a small volume of sample in conjunction with the analysis of such a sample to determine its organic carbon loading.

BRIEF DESCRIPTION OF THE DRAWINGS

Further objects and advantages of the present invention may be readily determined by reference to the following description and appended drawing, which are offered by way of example only and not in limitation of the invention, the scope of which is defined in the appended claims and by equivalents to the structure, materials, and acts set forth hereinafter.

In the drawings.

DETAILED DESCRIPTION OF THE PREFERRED EMBODIMENT

Figure 1:
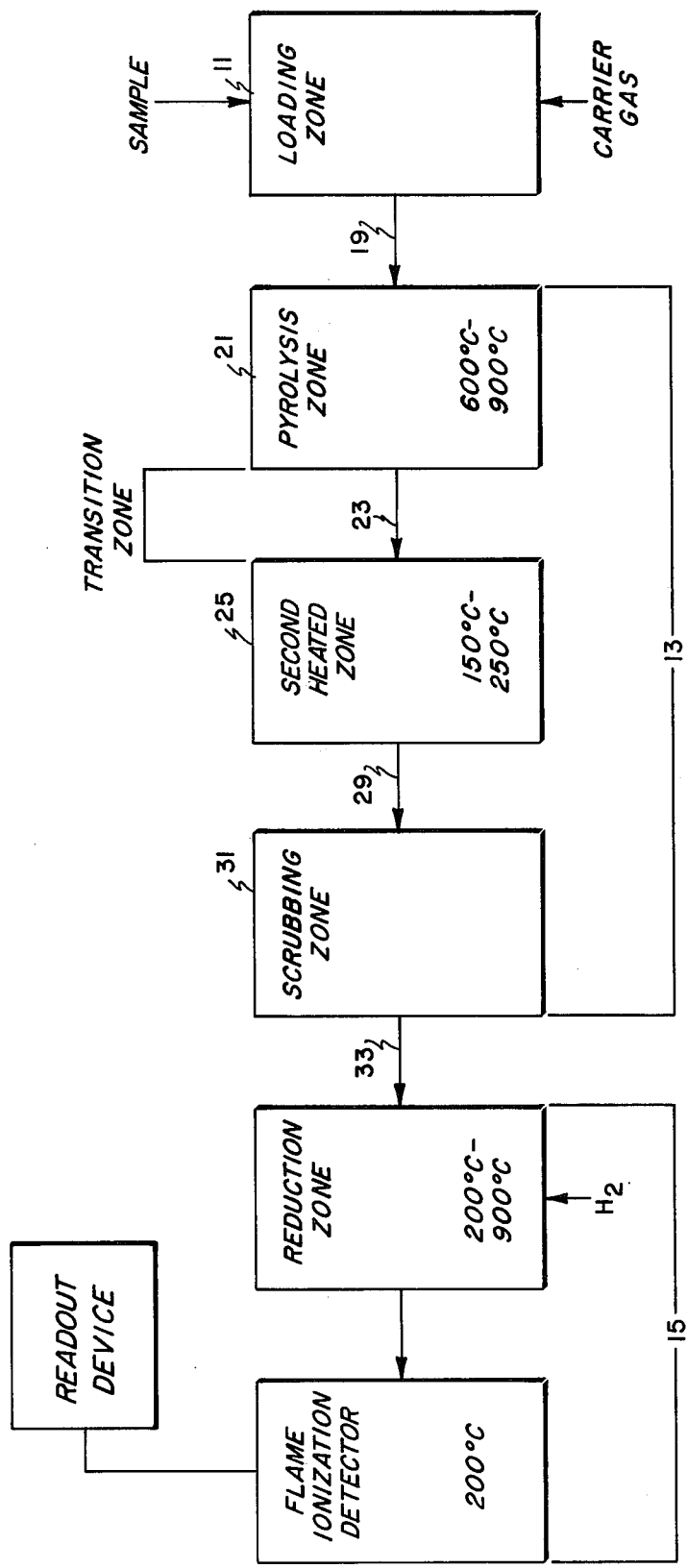
FIG. 1 is a schematic diagram of a system for practicing the present invention.

In the illustrated system there is generally provided a loading station 11 at which precisely measured sample quantities of sulfureous compounds or mixtures are introduced into a sealed chamber 13 wherein the samples are pyrolyzed and desulfurized, and then conveyed to an analysis device 15 wherein the organic carbon content of the gaseous pyrolysis products are quantitatively determined.

The equipment utilized at the sample loading station 11 is preferably of the type including small sample-carrying boats that are slidable within a sealed conduit and disposed for loading with metered quantities of sample injected by syringe through a septum seal or by an automatic valve, say of the slide type. Such loading equipment is available from Dohrmann Division of Envirotech Corporation, Santa Clara, California. Other types of conventional loading equipment can also be utilized. Normally, the boats are loaded at about room temperature.

From the loading station, the sample quantities are remotely moved in the aforementioned boats via a conduit 19 into a first or pyrolysis zone 21 in the chamber 13. This first zone is defined by a conventional pyrolysis furnace of the type wellknown in laboratory and test work. Preferably, the first zone is packed with a refractory metal oxide catalyst such as copperoxide, manganese-dioxide, vanadium-pentoxide, or cobalt-oxide in the form of wire, granules, or pellets. In practice, the first zone 21 is heated to about 600°–900° C to decompose the sulfureous samples in the presence of the catalyst to form sulfur dioxide and sulfur trioxide gases and vapors. At those elevated temperatures, organic materials in the samples are oxidized to form carbon dioxide gas; usually some elemental or low valent sulfur is also formed or already present.

From the pyrolysis zone 21, the sulfureous vapors and carbon dioxide gas are conveyed through a conduit 23 across a cooling transition or temperature gradient zone and then preferably into a second heated zone 25 that is packed with metal granules or wire which react with low valent sulfur molecules entrained in the carrier gas stream to form a solid sulfide compound that is absorbed onto the surface of the packing and thus removed from the flow stream. Normally, the second heated zone 25 is maintained at temperatures ranging from about 150°–250° C but the temperatures therein could be as low as 105° C and as high as 350° C. Typically, the conveyance into the second zone and there beyond in the chamber 13 is accomplished by introducing a pressurized stream of inert gas such as helium or argon into the system say at the loading zone 11, to entrain the aforementioned gaseous pyrolysis products.

Preferably the sulfur-removing packing in the second heated zone 25 in the chamber 13 is silver but the following other metals can be used: tin, lead, cobalt, nickel, zinc, cadmium, manganese, and iron.

Following the free sulfur removal operation, the remaining gases and vapors pass from the second heated zone via a sealed conduit 29 into a "scrubbing" zone 31 wherein the sulfur dioxide and trioxide vapors are selectively removed as will be described hereinafter in detail.

Following the scrubbing stage, the gaseous phase generally consists of carbon dioxide, water vapor and the inert carrier gas. Those gases and vapors then pass, via a third conduit 33, into the analysis device 15 which comprises conventional quantitative analysis equipment for determining the carbon content of the gases. The analysis equipment is preferably of the type wherein the carbon dioxide gas is mixed with a stream of hydrogen and reduced at an elevated temperature (say, 200°–900° C) in the presence of a reducing or hydrogenation catalyst, typically made of nickel, to effect an essentially complete conversion of the carbon dioxide gas to methane gas, $CH_4$, whose concentration is then determined by a conventional flame ionization detector to provide a measure of carbon content. As another example, the analysis equipment can comprise an infrared radiation detection device that quantitatively determines the carbon-dioxide concentration by measuring the spectral adsorption of the gaseous sample. The carbon content is shown or indicated on an instrument-compatable readout device.

In the following, the chemical reactions which occur in the first or pyrolysis zone 21 will be explained for the case where the initial sample is predominantly sulfuric acid, $H_2SO_4$. First, the sulfuric acid decomposes because of the heat to yield sulfur trioxide gas, $SO_3$, and water vapor in accordance with the following reaction: $H_2SO_4 \xrightarrow{330°C} SO_3 + H_2O$. Also, organic materials designated by the letter R hereinafter, are sulfonated by the sulfur trioxide gas as follows: $RH + SO_3 \rightarrow RSO_3H$. As the substances in this zone reach higher temperatures, the sulfonated materials are fragmented as follows:

$$RSO_3H \xrightarrow{\geq 350°C} SO_2, H_2O, R'H$$
$$RH \xrightarrow[Pt]{\geq 500°C} HC\equiv CH, CH_3\cdot, C_2\cdot, H\cdot, H_2$$

where R'H decomposes as RH. Where the pyrolysis zone catalyst is copper oxide, for example, the fragments formed in the preceding reactions are oxidized on the copper oxide in a series of reactions as follows as the temperatures in the pyrolysis zone 21 rise to about 600°–900° C:

$$HC\equiv CH + 10\,CuO \xrightarrow{\Delta} H_2O + 2\,CO_2 + 5\,Cu_2O$$

$$2\,CH_3\cdot + 14\,CuO \xrightarrow{\Delta} 3\,H_2O + 2\,CO_2 + 7\,Cu_2O$$

$$C_2\cdot + 8\,CuO \xrightarrow{\Delta} 2\,CO_2 + 4\,Cu_2O$$

$$2H\cdot + 2\,CuO \xrightarrow{\Delta} H_2O + Cu_2O$$

$$H_2 + 2\,CuO \xrightarrow{\Delta} H_2O + Cu_2O$$

The cuprous oxide, $Cu_2O$, designated in the preceding equations is followingly converted to its initial oxidation state by reaction with excess sulfur trioxide: $SO_3 \, 30\,Cu_2O \rightarrow SO_2 + 2\,CuO$. That reaction is encouraged by the presence of free oxygen, $O_2$, generated in the manner expressed by the following equilibrium equation: $2SO_3 \rightleftharpoons 2SO_2 + O_2$; where the right-hand side of the equation is favored at elevated temperatures.

The overall series of reactions which occur in the pyrolysis zone 21 may be summarized as:

$$SO_3 + RH + H_2O \xrightarrow{CuO/\Delta} SO_2 + SO_3 + H_2O + CO_2$$

Thus, the gases which exit from the packed pyrolysis furnace are $CO_2$, $SO_2$, $SO_3$, water vapor and trace amounts of low valent sulfur which are generated during the decomposition reactions or present in the initial sample.

As previously mentioned, the gases from the pyrolysis zone 21 are carried to the second heated zone 25 via the conduit 23 that extends across a temperature transition zone. In practice, the transition zone merely comprises an area in the system where the conduit 23 is uninsulated and exposed to ambient air for several inches. Heat transfer from even such a short section has been found to be sufficient to lower the temprature of the pyrolyzed substances considerably.

The temperatures in the second heated zone 25 are carefully controlled and, as mentioned hereinbefore, normally range from 150°–250° C. Where the sulfur-removing packing in the second heated zone is silver, normally in the form of silver-plated copper granules, the following reaction occurs:

$$S + 2Ag \xrightarrow{240°C} Ag_2S$$

The free sulfur-removal reaction is important because, otherwise, the sulfur could pass into the analysis zone 15 and poison the catalyst therein. Following the sulfur-removal reaction, the remaining gases pass into the aforementioned scrubbing zone 31.

The scrubbing zone contains a transition metal amine complex such as copper or cobalt amine sulfate which reacts with the gases which enter the scrubbing zone to remove all of the sulfur oxides therefrom. Sulfates of chromium, manganese, iron, and cobalt will also perform satisfactorily in the scrubbing zone; those materials being characterized by having two available oxidation states. In practice, the amine complex is supported on diatomaceous earth that has been precleaned to remove proteins or other carbonaceous materials therefrom. In the embodiment where the scrubbing zone contains a copper amine complex, sulfur dioxide is oxidized to sulfur trioxide according to the following reaction:

$$SO_2 + 2Cu\,(NH_3)_4\,SO_4 \cdot H_2O \rightarrow 2[NH_4]_2\,SO_4 + [Cu(NH_3)_2]_2\,SO_4$$

Followingly, the sulfur trioxide is removed by the reaction:

$$2\,SO_3 + Cu\,(NH_3)_4\,SO_4 \cdot H_2O + H_2O \rightarrow 2\,(NH_4)_2\,SO_4 + CuSO_4$$

Sulfur oxides, even in concentrations as low as one part per million, could also poison the catalysts in the analysis zone 15 and the foregoing reactions are important insofar as the sulfur oxides are completely removed from the flow stream. A benefit of using a copper amine complex in the scrubbing zone is that the color of the starting complex is deep blue but the reduced form, $[Cu(NH_3)_2]_2\,SO_4$, is brown and the anhydrous copper sulfate form, $CuSO_4$, is white. Thus, the color of the scrubbing zone provides an indication of the extent of depletion of the scrubbing material and, conversely, of the cummulative amount of sulfur which has entered the scrubber.

This indicating scrubber is also useful, for example, in a coal gasification process where the gasification products require a sulfur removal step prior to their reduction on a nickel catalyst.

Following the scrubbing zone, the sulfur-free gases pass into the analysis zone where their carbon content is quantitatively determined as hereinbefore described.

I claim:

1. A process for determining trace quantities of organic carbon in sulfureous mixtures and compounds comprising the steps of:

a. introducing small predetermined sample quantities of sulfureous matter into a first zone of a sealed chamber;

b. heating the introduced matter in the first zone to a temperature sufficient to decompose the matter to form sulfur dioxide and sulfur trioxide gases and to oxidize organic substances in the matter to form carbon dioxide gas;

c. conveying aforementioned gases from the first zone to subsequent zones in the chamber;

d. scrubbing the gases from the first zone in a scrubbing zone by the usage of a transition metal amine complex which reacts to remove sulfureous compounds from the gases without reaction with carbon dioxide gas; and e. analyzing the gases which exit from the scrubbing zone to determine the carbon dioxide content of the gases.

2. A process according to claim 1 wherein the introduced matter in the first zone is heated to a temperature ranging from 600°-900° C.

3. A process according to claim 1 wherein the transition metal amine complex consists of copper amine sulfate.

4. A process according to claim 1 wherein said transition metal amine complex is selected from the group consisting of sulfates of copper, chromium, manganese, iron, and cobalt.

5. A process according to claim 1 wherein heating of the introduced matter in the first zone is conducted in the presence of an inert gas.

6. A process according to claim 1 wherein heating of the introduced matter in the first zone is conducted in the presence of a refractory metal oxide catalyst.

7. A process according to claim 6 wherein the refractory metal oxide catalyst is selected from the group consisting of copper-oxide, manganese-dioxide, vanadium-pentoxide, and cobalt-oxide.

8. A process according to claim 1 wherein the introduced matter includes a sulfureous acid.

9. A process according to claim 8 wherein the sulfureous acid includes sulfuric acid.

10. A process according to claim 1 further including the step of cooling the gases from said first zone to a temperature ranging from 105° C to 350° C in a second zone and removing free sulfur therefrom on a sulfur-removing packing before passing the gases to a scrubbing zone.

11. A process according to claim 10 wherein the temperatures maintained in said second zone range from 105° C to 250° C.

12. A process according to claim 10 wherein the sulfur-absorbing packing disposed within the second zone is silver.

13. A process according to claim 10 wherein the sulfur-absorbing packing is selected from the group consisting of silver, tin, lead, cobalt, nickel, zinc, cadmium, manganese, and iron.

* * * * *